United States Patent [19]
Kato et al.

[11] Patent Number: 5,792,507
[45] Date of Patent: Aug. 11, 1998

[54] LACTOSE SPHERICAL PARTICLES AND PROCESS FOR THEIR PRODUCTION

[75] Inventors: Hisayoshi Kato; Nagayoshi Myo, both of Tokyo, Japan

[73] Assignee: Freund Industrial Co., Ltd., Tokyo, Japan

[21] Appl. No.: 788,588

[22] Filed: Jan. 24, 1997

[30] Foreign Application Priority Data

Jan. 24, 1996 [JP] Japan .................................. 8-028697
Jan. 7, 1997 [JP] Japan .................................. 9-011910

[51] Int. Cl.$^6$ .............................. B05D 1/38; B05D 1/40; B05D 1/02
[52] U.S. Cl. .................. 427/2.18; 427/2.15; 427/213; 427/214; 427/240; 427/242; 427/378
[58] Field of Search .................. 427/2.18, 2.15, 427/213, 214, 240, 242, 348, 378, 203, 424; 426/471

[56] References Cited

U.S. PATENT DOCUMENTS

| | | | |
|---|---|---|---|
| 2,661,294 | 12/1953 | Meade | 426/471 |
| 3,639,170 | 2/1972 | Hutton et al. | 426/471 |
| 3,908,045 | 9/1975 | Alterman et al. | 427/213 |
| 4,556,175 | 12/1985 | Motoyama et al. | 241/57 |
| 4,684,534 | 8/1987 | Valentine | 427/2.16 |
| 4,834,299 | 5/1989 | Kishibata et al. | 241/5 |
| 5,132,142 | 7/1992 | Jones et al. | 427/2.15 |
| 5,296,265 | 3/1994 | Okuma et al. | 427/213 |
| 5,505,983 | 4/1996 | Kamada | 427/2.16 |
| 5,507,871 | 4/1996 | Morino et al. | 118/680 |
| 5,618,562 | 4/1997 | Saito et al. | 424/489 |

*Primary Examiner*—Diana Dudash
*Attorney, Agent, or Firm*—Abelman, Frayne & Schwab

[57] ABSTRACT

To provide spherical particles made substantially from lactose and having high surface smoothness with low abrasiveness, and a process for their production.

A process for producing spherical particles containing at least 95 wt % lactose, characterized by comprising a step of producing lactose spherical particles by charging crystalline lactose and/or lactose granules onto a rotary disk in the treatment vessel of a centrifugal tumbling apparatus, dispersing powdered lactose to the lactose granules and/or crystalline lactose as the rotary disk is rotated while providing slit air into the vessel, while also spraying water, an aqueous lactose solution or a dilute aqueous solution of a water-soluble polymer, and a fixation treatment step of drying the obtained spherical particles in a fluidized bed apparatus while spraying an aqueous lactose solution and/or a dilute solution of a water-soluble polymer.

15 Claims, 4 Drawing Sheets

LACTOSE SPHERICAL PARTICLES AND PROCESS FOR THEIR PRODUCTION

BACKGROUND OF THE INVENTION

1. Technical Field of the Invention

The present invention relates to lactose spherical particles with high surface smoothness and low abrasiveness, and to a process for their production.

2. Description of the Related Art

Spherical particles used as raw materials for medicines are mainly utilized as seeds for sustained release preparations or enteric coated preparations. Examples of such spherical particles for preparations include "sugar spheres" made mainly from sucrose/starch which are listed in the "NF" (National Formulary), and purified sucrose (Nonpareil-103, tradename of Freund Industrial Co., Ltd.), purified sucrose/starch mixture (Nonpareil-101, tradename of Freund Industrial Co., Ltd.) and micro-crystalline cellulose spheres (Celpher, tradename of Asahi Chemical Industry Co., Ltd.) which are listed in the Supplement To Japanese Pharmaceutical Excipients 1993.

All of the substances serving as raw materials for such spherical particles have a physicochemical nature suited for sphere formation, and for example, although the cores of the group of spherical particles under the aforementioned tradename "Nonpareil" consist of granulated sugar in the form of monoclinic system with octahedrons or dodecahedrons, their aqueous solutions are suited for sphere formation because of the effective action as a binder, and while the product under the tradename "Celpher" consists of spherical particles without a core, the substance can easily be formed into spheres since the raw component of microcrystalline cellulose consists of short fibers.

Conventionally, the product under the aforementioned tradename "Nonpareil-103" has been produced by charging granulated sugar into a centrifugal tumbling apparatus (CF granulator, tradename of Freund Industrial Co., Ltd., hereunder abbreviated to "CF apparatus") and dispersing fine powdered sucrose to coat the granulated sugar nucleus, while spraying an aqueous sucrose solution as a binder, to thus form spherical granules. Likewise, the product under the aforementioned tradename "Nonpareil-101" has been produced by charging granulated sugar into a CF granulator and dispersing a fine powdered mixture of sucrose and starch to coat the granulated sugar nucleus, while spraying an aqueous mixture of sucrose and starch as a binder, to thus form spherical granules.

Another method of granulation from nuclei is disclosed in Japanese Unexamined Patent Publication No. 5-229961, as a process for producing spherical particles with a diameter of 0.1–1 mm made from a mixture of a water-soluble substance such as lactose and a water-insoluble substance such as microcrystaline cellulose.

These spherical particles can all be used as spherical particles for preparations, but since many drug agents also undergo Maillard reaction with the raw substances of the spherical particles in the preparation, complicated testing is required to confirm their compatibility with such drugs agents.

On the other hand, lactose has received attention as a material for producing spherical particles for preparations because it is a substance with very low reactivity and thus seldom undergoes Maillard reaction with drug agents; for example, in Japanese Unexamined Patent Publication No. 6-205959 there are disclosed spherical particles and a process for their production, which particles contain at least 95 wt % lactose, have a major diameter/minor diameter ratio of 1.2 or less, and in aggregate form having an bulk density of at least 0.7 g/ml and an angle of repose of 35 degrees or less.

Problems to be Solved by the Invention

Nevertheless, in the case of lactose spherical particles with low reactivity with drug agents, past efforts to create spherical particles of such lactose alone with high sphericalness and low abrasiveness have not been successful, because the lactose itself has no function as a binder.

For example, considering the production process disclosed in Japanese Unexamined Patent Publication No. 5-229961, although macroscopically spherical particles are obtained when the lactose and microcrystalline cellulose are combined at a mixing ratio of at least 95% lactose, when a scanning electron microscope is used to view the surface microscopically, the lactose powder is found clinging unevenly to the surface, and thus when the spherical particles are further coated with a drug agent to produce a sustained release preparation, the unevenness leads to greater abrasiveness and thus unavoidable reduction in yields (coating efficiency or granulating efficiency).

Likewise, in the case of the production process disclosed in Japanese Unexamined Patent Publication No. 6-205959 as well, it has been found by the present inventors that a lactose content of 95% or greater produces a phenomenon of microscopic roughness on the surface of the spherical particles.

It is an object of the present invention to provide novel spherical particles consisting substantially only of low-reactivity lactose and a production process therefore, which overcome the problems associated with conventional spherical particles which use sucrose (or a mixture of sucrose and starch), microcrystalline cellulose, lactose and microcrystalline cellulose mixtures, etc. as raw materials.

Means for Solving the Problems

The present inventors have conducted further research aimed at increasing the surface smoothness and lowering the abrasiveness of spherical particles consisting substantially of lactose and, as a result have completed the present invention upon the establishment of a production process whereby an aqueous lactose solution is sprayed in a fluidized bed onto spherical particles produced in the aforementioned CF apparatus, and dried to accomplish fixation treatment on the surface of the spherical particles.

In other words, the present invention relates to spherical particles characterized by containing at least 95 wt % lactose, having a major diameter/minor diameter ratio of 1.2 or less, and in aggregate form having an bulk density of at least 0.7 g/ml, an angle of repose of 35 degrees or less and an abrasiveness of 1.0% or less.

The present invention also relates to a process for producing lactose spherical particles with the characteristics described above, comprising a step of producing spherical particles by using crystalline lactose and/or lactose granules as nuclei and charging these nuclei onto a rotary disk in the treatment vessel of a centrifugal tumbling apparatus, dispersing powdered lactose to the microcrystalline lactose and/or lactose granules as the rotary disk is rotated while providing slit air into the vessel, while also spraying one selected from water, an aqueous lactose solution or a dilute aqueous solution of a water-soluble polymer, and a fixation treatment step of drying the obtained spherical particles in a fluidized bed apparatus while spraying an aqueous lactose solution and/or a dilute solution of a water-soluble polymer.

Best Mode for Carring Out the Invention

The lactose used according to the present invention is preferably a suitable type according to the lactose standards of the Pharmacopoeia of Japan (hereunder abbreviated to Pharmacopoeia) (e.g., 12th Edition of Pharmacopoeia, 2nd Supplement) when used for drugs, but it is not restricted thereto. For example, instead of α-lactose, β-lactose or mixtures thereof may be used.

Powdered lactose used according to the invention is lactose powder of pass through a sieve of 75 μm, and preferably it is of smaller than 1/10 the average particle size of the crystalline lactose or lactose granules serving as the nuclei. Powdered lactose of smaller particle size is preferred, and fine crystalline lactose may also be used.

The crystalline lactose serving as the nuclei according to the invention is crystalline lactose with a particle size of at least pass through a sieve of 75 μm, and crystalline lactose with a particle size of pass through a sieve of 300 μm, no pass through a sieve of 150 μm is particularly preferred. A larger particle size of the crystalline lactose gives spherical particles with a larger size.

Lactose granules according to the invention are obtained by granulating powdered lactose.

The major diameter/minor diameter ratio of the lactose spherical particles of the invention is the ratio of the major axis and minor axis of the spherical particles, which is a measure of the sphericalness. The ratio of the major axis and minor axis is determined by pouring the spherical particles randomly over a glass slide, photographing them, and measuring the length of the long axis (major diameter) and the length of the short axis (minor diameter) taken vertical to the center of the major axis, for 50 spherical particles, calculating the ratio of the major diameter to the minor diameter for each, and taking the average value for the 50 particles. Said ratio means aspect ratio.

The bulk density of the lactose spherical particles of the invention is the value obtained by measuring the weight Wb of a levelled amount of spherical particles in a 100 ml graduated cylinder (weight W) after lightly filling it to overflowing, according to the formula (Wb−W)/100, and it is expressed as the average value of 5 measurements.

The angle of repose for the lactose spherical particles of the invention is measured by the method of Nokami and Sugihara described in Japanese Unexamined Patent Publication No. 6-205959, and is expressed as the average value of 5 measurements. As shown in FIG. 2, the measuring device is an apparatus made by joining 4 glass plates of the size shown in the drawing: the repose angle is measured with this apparatus by using a funnel to gently pour in about 200 ml of a sample along side A onto side B as the glass bottom, continuing to pour until the sample begins to pour out from the front open end of side B, and determining the repose angle by using a protractor to read the angle formed against side B (horizontal surface) by the inclined surface of the sample layer on side B at the point at which the sample beings to pour out.

The abrasiveness of the lactose spherical particles of the invention is a numerical value for the degree of abrasion of the particle surface which occurs without destruction of the particles, upon impact by contact between the particles or between the particles and the vessel wall. It is measured by placing a prescribed amount of particles in the vessel, inducing rotatory or vibratory movement, removing them after a given period of time, separating the abraded and peeled powder with a sieve, and determining their weight with respect to the original weight, with the ratio expressed as a percentage.

As a concrete example of abrasiveness measurement, the weight Wt of spherical particles (about 10 g) is precisely measured and they are placed in a 32 mm inner diameter×65 mm depth stainless steel cylindrical vessel, after which a SPEX mixer mill is used for agitation at 1100 rpm for exactly 10 minutes, and the particles are then transferred to a #500 (300 μm) sieve for sifting, upon which the residual weight Ws (g) is precisely measured, and the following equation is used to calculate the abrasiveness.

$(Wt-Ws)/Wt \times 100 = \%$

The abrasiveness is generally preferred to be no greater than 1.0%, and is more preferably no greater than 0.5%.

The fixation treatment employed in the production process for the lactose spherical particles of the invention is treatment for smoothing the surface of the spherical particles.

Water-soluble polymers which may be used for the lactose spherical particles of the invention include, but are not limited to, animal polymers such as gelatin and casein; vegetable polymers such as alginic acid, carrageenan and hemicellulose; cellulose polymers such as carboxymethyl cellulose, methyl cellulose, hydroxyethyl cellulose, hydroxypropyl cellulose and hydroxypropylmethyl cellulose; synthetic polymers such as polyvinylpyrrolidone, polyacrylate and polyvinyl alcohol; and pullulan.

The water-soluble polymer is used in the form of a dilute aqueous solution. The concentration of the dilute aqueous solution of the water-soluble polymer is experimentally determined for each water-soluble polymer to weaken the binding force of the water-soluble polymer as a binder (see Example 3 and Comparative Example 3).

The active ingredient which can be carried in the lactose spherical particles of the invention is any substance which has a effects as drug. It may be appropriately selected from among many different types including water-soluble vitamins, analgesic antipyretics, and the like.

The centrifugal tumbling apparatus used for production of the lactose spherical particles of the invention has a smooth rotary disk which rotates substantially horizontally on the bottom of the treatment vessel; a rotary shaft around which the rotary disk rotates; a slit which is the ring-shaped space formed between the inner wall section of the treatment vessel and the edge of the rotary disk at the point of its perimeter; a slit air feeding apparatus for feeding slit air into the treatment vessel through the slit; a spray nozzle for spraying at least one selected from water, an aqueous lactose solution or a dilute aqueous solution of a water-soluble polymer into a substance to be treated (crystalline lactose or lactose granules) in the treatment vessel; and a powder dispersing apparatus for dispersing the powder into the substance being treated. An embodiment of such an apparatus is a CF granulator (hereunder abbreviated to CF apparatus) manufactured by Freund Industrial Co., Ltd. as shown in FIG. 1 (with the slit air feeding apparatus not shown).

The CF apparatus belongs to a category known as granulating-coating apparatuses, and is not limited to the specific CF apparatus described above, as various other types of granulating-coating apparatuses may be used so long as they have the designated basic structure. Many different modifications of the CF apparatus are possible, including mounting of the rotary shaft on the rotary disk, or using a flat type of rotary disk instead of one with the edge curved upward, and although at least the upper side of the rotary disk which is in contact with the powder must be smooth, the center section of the disk may have protrusions.

The fluidized bed apparatus of the present invention has a holding vessel to contain the spherical particles produced by the centrifugal tumbling apparatus, an air feeder to feed fluidizing air to induce fluidizing the spherical particles, and a spray nozzle to spray the aqueous lactose solution and/or dilute water-soluble polymer solution onto the spherical particles; for example, a "Flow Coater" (hereunder abbreviated to "FL apparatus"), tradename of Freund Industrial Co., Ltd. may be used. This apparatus belongs to the category of fluidized bed granulating-coating apparatuses, and is not limited to the aforementioned specific FL apparatus so long as it has the basic construction according to the invention, as other fluidized bed apparatuses equipped with rotary disk with aerated sections may also be used. (For example, an FL apparatus equipped with a rotary disk or centrifugal fluidized granulating-coating apparatus, tradename "SPIR-A-FLOW", manufactured by Freund Industrial Co., Ltd.)

The solution sprayed in the centrifugal tumbling apparatus used for production of the lactose spherical particles of the invention may be water alone or, if desired, a small amount of a water-soluble polymer may be dissolved therein, or an aqueous lactose solution may be added, in which case the solution may also contain a small amount of an added coloring agent. However, water alone is usually preferred.

A process for producing lactose spherical particles according to the invention will now be explained with reference to the CF apparatus shown in FIG. 1.

In this drawing, numeral 1 is a granulating vessel, 2 is a rotary disk, 2a is the disk edge, 3 is a rotary shaft, 4 is a slit, 4a is slit air, 5 is an air chamber, 6 is a dehumidifier, 7 is a heat-exchanger, 8 is powder, 9 is a dispersing apparatus, 10 is spraying liquid, 11 is a tank, 12 is a constant flow pump, 13 is a spray nozzle, 14 is spraying air, 15 is a product ejection apparatus, 16 is a stator cover, and 17 is air for the slit air.

In the CF apparatus of FIG. 1, the rotary shaft 3 is rotated by a driving mechanism such as a motor (not shown), and air 17 passing through the dehumidifier 6 and heat-exchanger 7 passes through the air chamber 5 while the rotary disk 2 is rotated, and is fed to the granulating vessel 1 from the slit 4 as slit air 4a, while crystalline lactose is poured onto the rotary disk.

Powdered lactose 8 is simultaneously dispersed from the dispersing apparatus 9 near the edge 2a where the slit air 4a is blown in, while water 10 is sprayed from the tank 11 through the spray nozzle 13 onto the powdered lactose layer near the slit. This accomplishes granulation to produce moist lactose spherical particles.

The moist lactose spherical particles produced in this manner are then sent to an FL apparatus (not shown), where they are subjected to fixation treatment involving coating and drying under conditions of a sprayed solution, such as an aqueous lactose solution, while in a state of fluidizing induced by an air flow, to produce as the final product lactose spherical particles with the characteristics described above.

EXAMPLES

The present invention will now be explained in more detail by way of the following examples which, however, are not intended to be restrictive.

Example 1

Using the centrifugal tumbling granulator ("Model CF-360" manufactured by Freund Industrial Co., Ltd.) shown in FIG. 1, 500 g of 212–425 µm crystalline lactose was charged in while feeding slit air, and the rotary disk was rotated at 200 rpm.

Next, 2000 g of powdered lactose with an average particle size of 12.5 µm was dispersed therein at a feeding rate of 60 g/min, and 375 ml of water was splayed under a pressure of 0.8 kg/cm$^2$ for 46 minutes (for granulation) to obtain moist lactose spherical particles.

The resulting moist lactose spherical particles were placed in a fluidized bed granulator ("Model FLO-5", tradename of Freund Industrial Co., Ltd.) and dried at 60° C. while spraying (for coating) 625 g of a 20 wt % aqueous lactose solution at a rate of 40 ml/min. Spherical particles of 500–710 µm were obtained at a yield of 79.5%. The major diameter/minor diameter ratio of the spherical particles was 1.09, the bulk density was 0.75 g/ml, and the angle of repose was 32°. The surface of the spherical particles had satisfactory surface smoothness, as shown by the scanning electron microscope image in FIG. 5. The abrasiveness was 0.30%.

The cross-section of the lactose spherical particles of this example with a crystalline lactose nucleus shows a "spear tip-shaped" form around a center of spherical particles with a size of about 715 µm, as shown by the electron microscope image in FIG. 3, showing that powder lactose had adhered and fixed around the outside, forming true spherical lactose spherical particles.

Measurement of the physical characteristics of the spherical particles according to the standard for NFl8 "Lactose Monohydrate" resulted in a 0.2% loss on drying and 5.0% water, and thus the standards were met.

Example 2

In the same manner as Example 1, 500 g of 180–300 µm crystalline lactose was charged into a Model CF-360 after admitting slit air, and the rotary disk was rotated at 200 rpm. Next, 1500 g of powdered lactose with an average particle size of 12.5 µm was dispersed therein at a feeding rate of 60 g/min, while spraying water at a pressure of 0.8 kg/cm$^2$ and at a rate of 10 ml/min for granulation. Upon complete dispersion of the powdered lactose, 50 ml of a 20 wt % aqueous lactose solution was sprayed at a rate of 10 ml/min.

The resulting moist spherical particles were placed in a Model FLO-5 (fluidized bed granulator, product of Freund Industrial Co., Ltd.) for fluidized drying at 60° C. After completion of drying, 450 g of a 20 wt % aqueous lactose solution was sprayed and dried at a rate of 40 ml/min under the same flow conditions, to accomplish coating. This method gave 355–500 µm spherical particles consisting substantially of lactose alone, at a yield of 71.5%. The major diameter/minor diameter ratio of the spherical particles was 1.1, the bulk density was 0.77 g/ml, and the angle of repose was 33°. The surface had satisfactory surface smoothness, similar to the particle shown in FIG. 5. The abrasiveness was 0.32%.

Example 3

The moist spherical particles obtained in Example 2 were placed in a Model FLO-5 fluidized bed granulator and dried at 60° C. After completion of drying, 400 g of a 2.5 wt % aqueous solution of hydroxypropyl cellulose (HPCL, tradename of Nippon Soda, Co., Ltd.) was sprayed and dried at a rate of 20 ml/min for coating. This method gave 355–500 µm spherical particles at a yield of 73.4%. The major diameter/minor diameter ratio of the spherical particles was 1.1, the bulk density was 0.76 g/ml, and the angle of repose was 33°.

The surface had the same satisfactory surface smoothness as shown in FIG. 5. The abrasiveness was 0.28%.

Comparative Example 1

The moist spherical particles obtained in Example 1 were placed in a Model FLO-5 fluidized bed granulator and dried at 60° C. This method gave 500–710 μm spherical particles at a yield of 82.5%. The major diameter/minor diameter ratio of the spherical particles was 1.10, the bulk density was 0.74 g/ml, and the angle of repose was 33°.

The surface condition had powdered lactose with a major diameter on the order of a few tens of μm adhered to the surface of spherical particles with a diameter of 720 μm, as shown in FIG. 4. Although the values for the bulk density and angle of repose of the spherical particles were acceptable, the inadequate surface smoothness created high abrasiveness. The abrasiveness was 8.1%.

Comparative Example 2

250 g of crystalline lactose with an average particle size of 200 μm was charged into a centrifugal tumbling granulator (Model CF-360, tradename of Freund Industrial Co., Ltd.), and the rotary disk was rotated at 220 rpm. Next, 600 g of powdered lactose with an average particle size of 40 μm was dispersed therein, and 1 kg of a 40 wt % aqueous lactose solution was sprayed for an hour. Spherical particles 420μm–300 μm in size were obtained at a yield of 82.4%. The major diameter/minor diameter ratio of the spherical particles was 1.11, the bulk density was 0.79 g/ml, and the angle of repose was 31.7°.

The surface condition lacked surface smoothness similar to the particle shown in FIG. 4, and powdered lactose with a particle size of a few tens of μm was abundantly adhered to the surface. The abrasiveness was 8.5%.

Comparative Example 3

Granulation and coating was performed with the same method and conditions as in Example 2, except that a 5 wt % aqueous solution was used instead of the 2.5 wt % aqueous solution of HPC-L used in Example 3. Since the resulting granules included much fine powder not adhering to the nuclei and the major diameter/minor diameter ratio of the particles was 1.2 or greater, the desired spherical particles could not be formed.

As seen by comparing Example 3 and Comparative Example 3, when the aqueous solution concentration of a water-soluble polymer such as HPC-L is raised to increase the binding strength, the height of the binding strength becomes an impediment, thus preventing formation of spherical particles.

Furthermore, as seen by comparison of the three examples in addition to Example 1, when a water-soluble polymer is used, lowering the aqueous solution concentration of the water-soluble polymer to weaken the binding strength results in formation of spherical particles.

Example 4

A product was prepared by kneading 100 ml of a 10 wt % aqueous HPC-L solution with 1 kg of powdered lactose which had passed through a 75 μm sieve, and this was extruded through a 0.5 mm screen to make granules for granulated lactose.

The granulated lactose was then dried to make particles, and a sieve was used to sort it into granulated lactose of particles sizes 500–710 μm.

Next, the same procedure as in Example 1 was conducted, except that granulated lactose was used instead of the crystalline lactose of Example 1 and 1800 g of powdered lactose was used instead of 2000 g of powdered lactose, by which 710–1000 μm spherical particles were obtained at a yield of 78.0%. The major diameter/minor diameter ratio of the spherical particles was 1.11, the bulk density was 0.76 g/ml, and the angle of repose was 33°. The surface of the resulting spherical particles had satisfactory surface smoothness, as shown by the scanning electron microscope image in FIG. 5. The abrasiveness was 0.35%.

Measurement of the physical characteristics of the spherical particles according to the standard for NF18 "Lactose Monohydrate" resulted in a 0.2% loss on drying and 5.2% water, and thus the standards were met.

Effect of the Invention

The spherical particles of the present invention consist mainly of lactose, and thus have advantages over conventional spherical particles using sucrose (or mixtures of sucrose and starch), including slower dissolution and resistance to disintegration, as well as having a lower calorie content. In addition, the spherical particles have ideal characteristics as nuclei for controlled-release drugs, since they do not have the problem of complete resistance to disintegration as do spherical particles composed mainly of crystalline cellulose, but instead have suitable disintegration properties.

Furthermore, since the lactose spherical particles of the invention have excellent surface smoothness and abrasion resistance as a result of fixation treatment of their surface, greater granulating and coating efficiency is possible for production of sustained-release preparations, etc., by which improved productivity and lower cost may be expected.

The particles may also be ideally designed for sustained-release preparations because the surface smoothing by fixation treatment provides a more uniform coating thickness of drugs or controlled-release layers coated onto the spherical particles, thus allowing control of the thickness of layers whose release rate depends on the thickness, and control of drug dosages to guarantee effective blood levels.

Since the spherical particles of the invention consist of lactose alone or contain a very high proportion of lactose, reaction with drug agents is minimized, which is advantageous when enclosing drugs in the spherical particles. Particularly in the case of a composition with lactose alone, the present invention for the first time provides the drug industry with surface-smooth spherical particles which could not be produced according to the prior art.

Moreover, since drug agents may be enclosed in the spherical particles, an unprecedented type of sustained-release agent is made possible, by combining 2 separate drug agent layers or controlled-release layers coating the spherical particles, thus preparing a 3-layer sustained-release agent, to design a controlled-release layer wherein the pH-dependency of the solubility is divided into stages.

Figure 1:
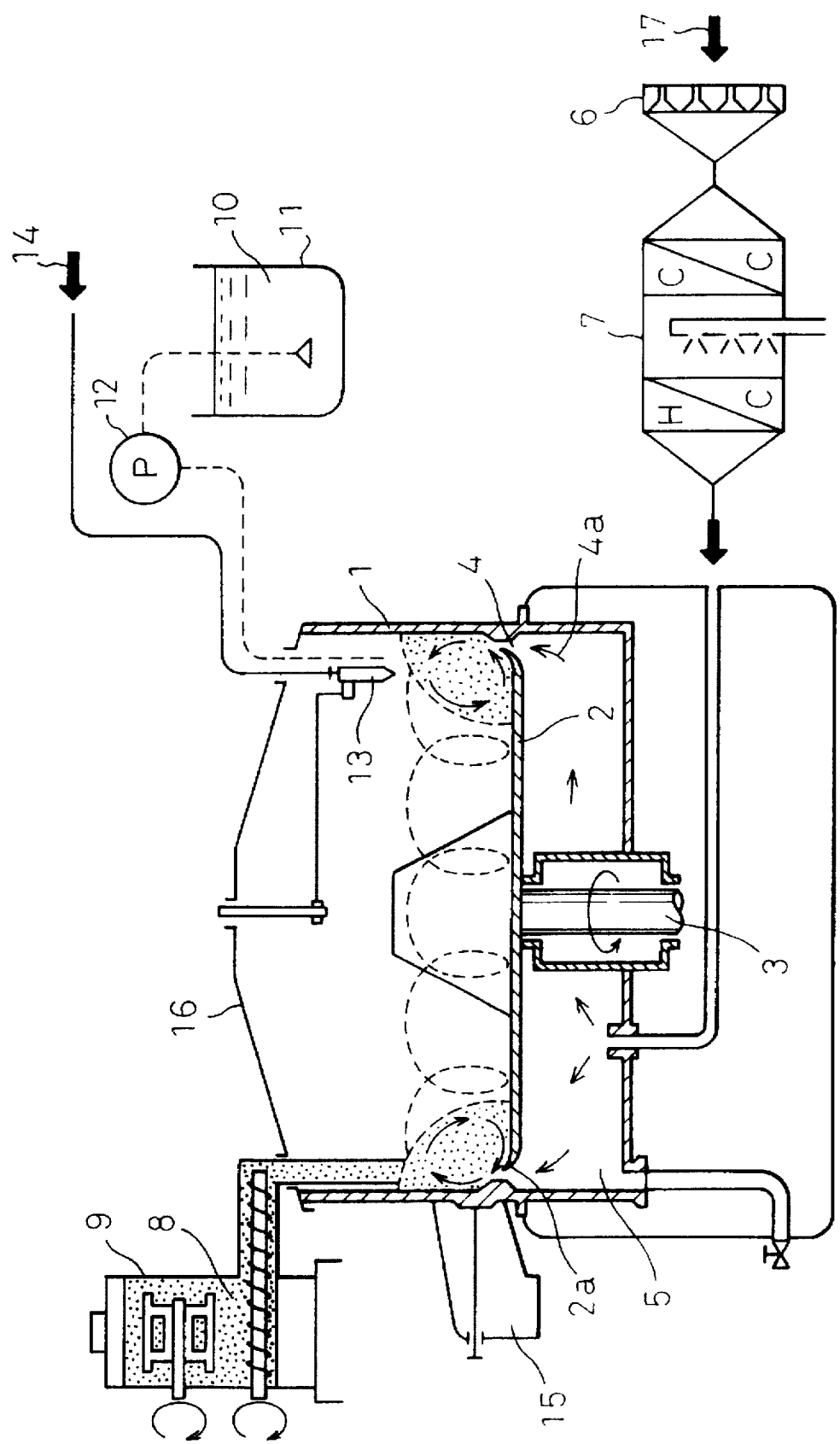
FIG. 1 shows an embodiment of a granulating-coating apparatus which may be used according to the invention.
Figure 2:
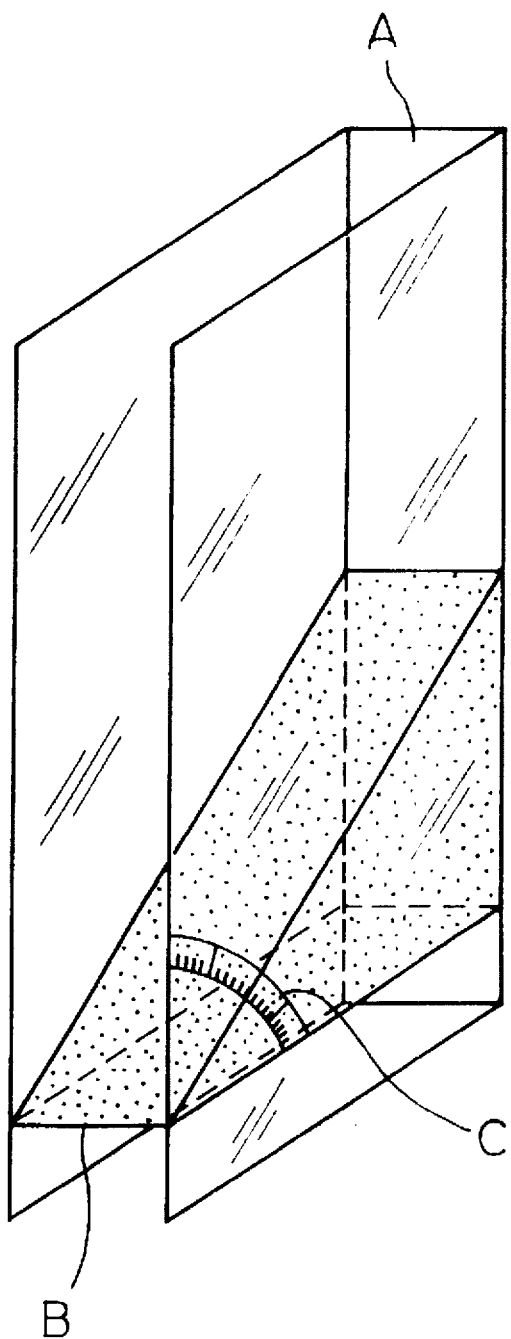
FIG. 2 is an illustration of a method for measuring the repose angle of lactose spherical particles.
Figure 3:
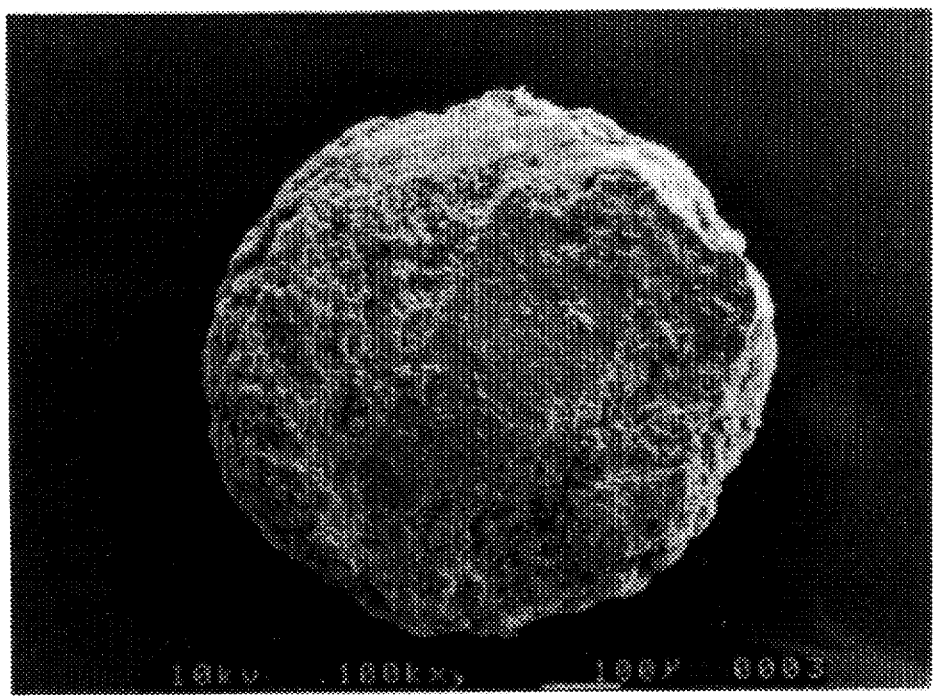
FIG. 3 is an image showing the cross-section of a lactose spherical particle according to the invention, as observed by an electron microscope.
Figure 4:
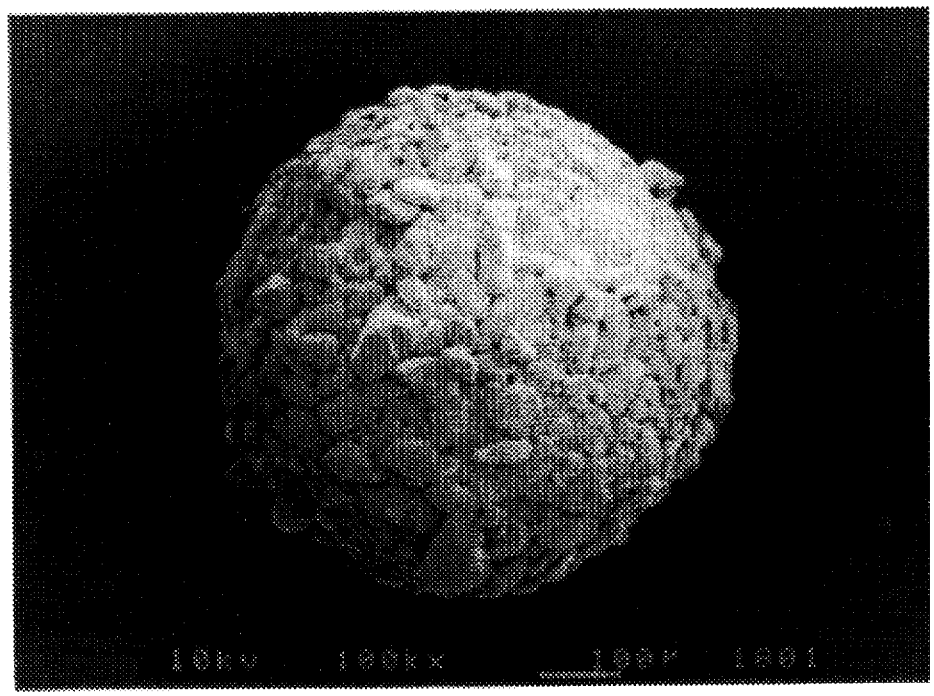
FIG. 4 is an image showing the surface condition of a lactose spherical particle having undergone no fixation treatment.
Figure 5:
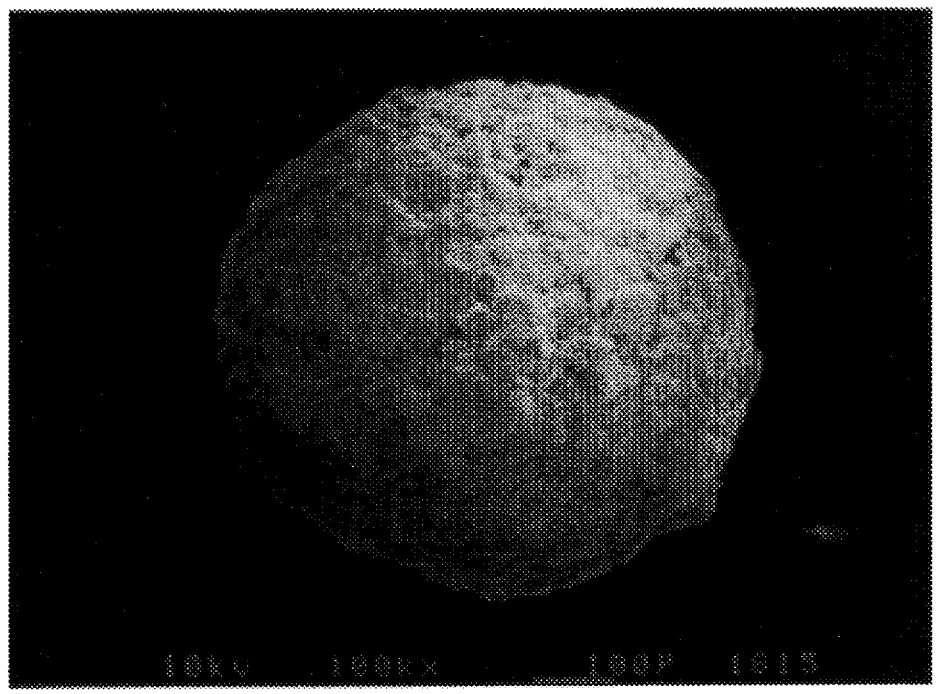
FIG. 5 is an image showing the surface condition of a lactose spherical particle according to the invention, as observed by an electron microscope.

EXPLANATION OF SYMBOLS 1 granulation vessel
2 rotary disk
2a disk edge
3 rotary shaft
4 slit
5 air chamber
6 dehumidifier
7 heat-exchanger
8 powder
9 dispersing apparatus
10 spraying liquid
11 tank
12 constant flow pump
13 spray nozzle
14 spraying air
15 product ejection apparatus
16 stator cover
17 air for slit air

We claim:

1. A process for producing spherical particles of improved surface smoothness containing at least 95 percent by weight of lactose comprising:

(a) charging particulate lactose material selected from the group consisting of crystalline lactose or lactose granules or a combination of crystalline lactose and lactose granules onto the rotary disk in the treatment vessel of a centrifugal tumbling apparatus, said disk being surrounded by a vessel wall;

(b) dispersing powdered lactose on said particulate lactose material as said rotary disk is rotated, (c) passing a stream of air from below said rotary disk through a slit between the periphery of said disk and the adjacent vessel wall;

(d) spraying said powdered lactose and said particulate lactose material with water solution and a dilute solution of a water-soluble until spherical particles are formed;

(e) drying said spherical particles while maintaining them in a fluidized bed; and (f) spraying said spherical particles in said fluidized bed with a liquid selected from the group consisting of an aqueous lactose solution or a solution of water-soluble polymer.

2. The process of claim 1 where the particle size of said crystalline lactose or said lactose granules is in the range from about 150–300 μm.

3. The process of claim 1 where said particle size of said crystalline lactose or said lactose granules is in the range from about 150–500 μm.

4. The process of claim 1 where said powdered lactose will pass a 75 μm screen.

5. The process of claim 1 where the particle size of said powdered lactose is smaller than one-tenth of the average particle size of said crystalline lactose or said lactose granules.

6. The process of claim 1 where the resulting spherical particles have an abrasiveness not exceeding one percent.

7. The process of claim 6 where the resulting spherical particles have an abrasiveness of less than 0.35%.

8. The process of claim 1 where the particles are, dried before the spraying of step (f).

9. The process of claim 1 where the solution in step (f) is aqueous lactose.

10. The process of claim 9 where the spherical particles are approximately 100% lactose.

11. The process of claim 9 in which the spherical particles consist essentially of lactose.

12. The process of claim 1 where the resulting spherical particles have a ratio of major particle diameter to minor particle diameter of 1.2 or less, a bulk density in aggregate form of at least 0.7 g/ml, an angle of repose of 35° or less, and an abrasiveness not exceeding one percent.

13. The process of claim 12 wherein said spherical particles comprise a water-soluble polymer.

14. The process of claim 12 in which the resulting spherical particles pass through a screen of 1400 μm and are held on a screen of 300 μm.

15. The process of claim 1 in which the resulting dried spherical particles have a moisture content of approximately one percent.

* * * * *

UNITED STATES PATENT AND TRADEMARK OFFICE
CERTIFICATE OF CORRECTION

PATENT NO.   : 5,792,507
DATED        : August 11, 1998
INVENTOR(S)  : Hisayoshi Kato It is certified that error appears in the above-identified patent and that said Letters Patent is hereby corrected as shown below:

In claim 1, delete paragraph (d) and substitute therefor:

"(d) spraying said powdered lactose and said particulate lactose material with water until spherical particles are formed;"

In claim 8, line 1 after "are" delete the comma.

Signed and Sealed this

Twenty-ninth Day of December, 1998

Attest:

BRUCE LEHMAN

Attesting Officer

Commissioner of Patents and Trademarks